United States Patent [19]

Robson et al.

[11] Patent Number: 5,208,239
[45] Date of Patent: May 4, 1993

[54] FUNGICIDAL PYRIDINYLPYRIMIDINE COMPOUNDS

[75] Inventors: Michael J. Robson, Bracknell; Paul A. Worthington, Maidenhead, both of England

[73] Assignee: Imperial Chemical Industries PLC, London, United Kingdom

[21] Appl. No.: 785,646

[22] Filed: Oct. 31, 1991

[30] Foreign Application Priority Data

Nov. 15, 1990 [GB] United Kingdom ............... 9024873

[51] Int. Cl.$^5$ ................. A61K 31/505; C07D 239/24; C07D 401/04
[52] U.S. Cl. .................... 514/256; 514/269; 544/289; 544/319; 544/322; 544/328; 544/333
[58] Field of Search ............. 544/333, 335, 289, 319, 544/322, 328; 514/256, 275, 269

[56] References Cited

U.S. PATENT DOCUMENTS

| | | | |
|---|---|---|---|
| 4,733,466 | 3/1988 | Fletcher, Jr. ............... | 30/34.2 |
| 4,752,608 | 6/1988 | Katoh et al. ............... | 514/269 |
| 4,783,466 | 11/1988 | Katoh et al. ............... | 544/333 |
| 4,873,248 | 10/1989 | Katoh et al. ............... | 514/269 |
| 4,927,827 | 5/1990 | Katoh et al. ............... | 544/256 |

FOREIGN PATENT DOCUMENTS

| | | |
|---|---|---|
| 0407899 | 1/1991 | European Pat. Off. . |
| 0431421 | 6/1991 | European Pat. Off. . |
| 0431424 | 6/1991 | European Pat. Off. . |
| 4001557 | 1/1990 | Fed. Rep. of Germany . |
| 3169803 | 11/1989 | Japan . |
| 3-169802 | 7/1991 | Japan . |
| 007399 | 5/1991 | World Int. Prop. O. . |
| 0007400 | 5/1991 | World Int. Prop. O. . |

OTHER PUBLICATIONS

Kato et al., Chemical Abstract, vol. 113, #172045m, 1990.
Kato et al., Chemical Abstract vol. 113, #128077z, 1990.
Kato et al., Chemical Abstract vol. 108 #56119m, 1988.

*Primary Examiner*—Mukund J. Shah
*Assistant Examiner*—Y. N. Gupta
*Attorney, Agent, or Firm*—William E. Dickheiser

[57] ABSTRACT

Fungicidal compounds having the formula (I):

wherein $R^1$ is an optionally substituted phenyl group, $C_{3-6}$ cycloalkyl optionally substituted by alkyl or alkyl; $R^2$, $R^3$, $R^4$, $R^5$, $R^6$ and $R^7$ are independently hydrogen, $C_{1-4}$ alkyl, $C_{1-4}$ haloalkyl, $C_{1-4}$ alkoxy or $N'R''$; Z is a linking group and is $-C\equiv C-$, $-CR^8=CR^{10}-$ or $-CR^8R^9-CR^{10}R^{11}-$; $R^8$, $R^9$, $R^{10}$, $R^{11}$, $R'$ and $R''$ are independently hydrogen or $C_{1-4}$ alkyl; provided that when R is alkyl Z is not $-CR^8R^9-CR^{10}R^{11}-$; and acid addition salts or metal complexes thereof; and processes for preparing then, compositions comprising them and methods of using them to combat fungi.

8 Claims, No Drawings

FUNGICIDAL PYRIDINYLPYRIMIDINE COMPOUNDS

The present invention relates to pyridylpyrimidine derivatives that are useful as fungicides, to processes for preparing them, to fungicidal compositions containing them, and to methods of using them to combat fungi, especially fungal infections in plants.

According to the present invention there is provided a compound having the general formula (I), wherein $R^1$ is an optionally substituted phenyl group, $C_{3-6}$ cycloalkyl optionally substituted by alkyl, or alkyl; $R^2$, $R^3$, $R^4$, $R^5$, $R^6$ and $R^7$ are independently hydrogen, $C_{1-4}$ alkyl, $C_{1-4}$ haloalkyl, $C_{1-4}$ alkoxy or $NR'R''$; Z is a linking group and is $-C\equiv C-$, $-CR^8=CR^{10}-$ or $-CR^8R^9-R^{10}R^{11}-$; $R^8$, $R^9$, $R^{10}$, $R^{11}$, $R'$ and $R''$ are independently hydrogen or $C_{1-4}$ alkyl; provided that when $R^1$ is alkyl Z is not $-C^8R^9-CR^{10}R^{11}-$; and acid addition salts or metal complexes thereof.

Alkyl groups and the alkyl moiety of the alkoxy group contain from 1 to 6, especially from 1 to 4, carbon atoms and are in the form of straight or branched chains, i.e. methyl, ethyl, n-propyl, iso-propyl, n-butyl, iso-butyl, sec-butyl or tert-butyl.

Halogen includes fluorine, chlorine, bromine and iodine atoms.

Haloalkyl groups contain from 1 to 4 carbon atoms and at least one halogen. They are in the form of either straight or branched chains and are, for example, fluoromethyl, chloromethyl, fluoroethyl, chloroethyl, trifluoromethyl, trichloromeihyl, pentafluoromethyl or hexafluoro iso-propyl.

Cycloalkyl contains from 3 to 6 carbon atoms and is, for example, cyclopropyl, cyclopentyl or cyclohexyl.

The acid addition salts of the compounds of the invention include salts with inorganic or organic acids, for example, hydrochloric, nitric, sulphuric, acetic, 4-toluene-sulphonic or oxalic acids.

The metal complexes of the compounds of the invention include complexes with copper, zinc or manganese cations.

Optional substituents on the phenyl group include halogen (especially chlorine, fluorine or bromine), $C_{1-4}$ alkyl (especially methyl), $C_{1-4}$ alkoxy (especially methoxy), $C_{1-4}$ haloalkoxy (especially trifluoromethoxy), $C_{2-4}$ alkenyl (especially vinyl or allyl), $C_{2-4}$ alkynyl (especially ethynyl or propargyl), $C_{1-4}$ haloalkyl (especially trifluoromethyl or mono- or di-($C_{1-4}$)alkylamino (especially methylamino or dimethylamino), or phenyl, benzyl, phenoxy oz benzyloxy optionally substituted with halogen (especially chlorine or fluorine), $C_{1-4}$ alkyl (especially methyl), $C_{1-4}$ haloalkyl (especially trifluoromethyl), $C_{1-4}$ alkoxy (especially methoxy) or $C_{1-4}$ haloalkoxy (especially trifluoromethoxy).

Alkenyl groups contain from 2–4 carbon atoms and are alk-1-enyl, alk-2-enyl or alk-3-enyl, for example, vinyl, 2-prop-1-enyl, 1-prop-1-enyl, allyl, 2-but-2-enyl, 1-(2-methylprop-1-enyl), 1-but-1-enyl, 1-(1-methylprop-2-enyl), 1-(2-methylprop-2-enyl), 1-but 2-enyl, or 1-but-3-enyl.

Alkynyl groups contain from 2 to 4 carbon atoms and are, for example, ethynyl, prop-1-ynyl, propargyl or 2-but-3-ynyl.

Compounds wherein Z is $-CR^8=CR^{10}-$ can exist as geometric isomers. The present invention covers both isomers and mixtures in any proportion of these isomers.

In one particular aspect the present invention provides a compound of general formula (I) wherein $R^1$ is an optionally substituted phenyl group (especially optionally substituted with halogen, $C_{1-4}$ alkyl, $C_{1-4}$ alkoxy, $C_{1-4}$ haloalkoxy, $C_{1-4}$ alkenyl, $C_{2-4}$ alkynyl, $C_{1-4}$ haloalkyl or phenyl); $R^2$, $R^3$, $R^4$, $R^5$, $R^6$ and $R^7$ are independently hydrogen, $C_{1-4}$ alkyl, $C_{1-4}$ haloalkyl or $C_{1-4}$ alkoxy; Z is a linking group and is $-C\equiv C-$, $-CR^8=CR^{10}-$ or $-CR^8R^9-CR^{10}R^{11}-$; $R^8$, $R^9$, $R^{10}$ and $R^{11}$ are independently hydrogen or $C_{1-4}$ alkyl; and acid addition salts or metal complexes thereof.

In another aspect the present invention provides a compound of general formula (I) wherein $R^1$ is an optionally substituted phenyl group, $C_{3-6}$ cycloalkyl optionally substituted by alkyl or alkyl; $R^2$, $R^3$, $R^4$, $R^5$, $R^6$ and $R^7$ are independently hydrogen, $C_{1-4}$ alkyl, $C_{1-4}$ haloalkyl, $C_{1-4}$ alkoxy or $NR'R''$; Z is $-CR^8=CR^{10}-$ or $-C\equiv C-$; $R^8$ and $R^{10}$ are independently $C_{1-4}$ alkyl or, preferably, hydrogen; $R'$ and $R''$ are independently hydrogen or $C_{1-4}$ alkyl; and acid addition salts or metal complexes thereof.

In a further aspect the present invention provides a compound of general formula (I) wherein $R^2$, $R^3$, $R^4$, $R^6$ and $R^7$ are all hydrogen and $R^5$ is $C_{1-4}$ alkyl (especially methyl).

In a still further aspect the present invention provides a compound of general formula (I) wherein $R^1$ is phenyl optionally substituted with halogen (especially fluorine, chlorine or bromine), $C_{1-4}$ alkyl (especially methyl), $C_{1-4}$ alkoxy especially methoxy), $C_{1-4}$ haloalkoxy (especially trifluoromethoxy), $C_{2-4}$ alkenyl (especially vinyl and allyl), $C_{2-4}$ alkynyl (especially ethynyl and propargyl), $C_{1-4}$ haloalkyl (especially trifluoromethyl) or phenyl; Z is $-C\equiv C-$; $R^2$, $R^3$, $R^4$, $R^6$ and $R^7$ are all hydrogen; $R^5$ is $C_{1-4}$ alkyl (especially methyl); and acid addition salts or metal complexes thereof.

In yet another aspect the present invention provides a compound of general formula (I) wherein $R^1$ is phenyl optionally substituted with halogen (especially chlorine), $C_{1-4}$ alkyl (especially methyl), $C_{1-4}$ haloalkoxy (especially trifluoromethoxy) or phenyl, or $R^1$ is cyclohexyl; Z is $-CH=CH-$ or $-C\equiv C-$; $R^2$, $R^3$, $R^4$, $R^6$ and $R^7$ are all hydrogen; and $R^5$ is $C_{1-4}$ alkyl (especially methyl).

In another aspect the invention provides compounds of formula (I) in which $R^1$ is a phenyl group, $R^2$, $R^3$, $R^4$, $R^6$ and $R^7$ are all hydrogen, $R^5$ is $C_{1-4}$ alkyl (especially methyl) and Z is $-C\equiv C-$ or $-CH=CH-$.

Examples of compounds of the invention of formula (I) are given in Table I.

TABLE I

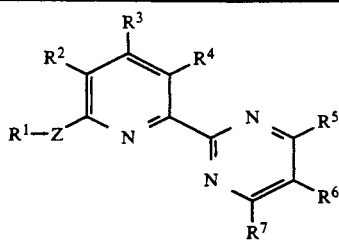

| Compound No | R¹ | R² | R³ | R⁴ | R⁵ | R⁶ | R⁷ | Z | mp °C | Comments |
|---|---|---|---|---|---|---|---|---|---|---|
| 1 | C₆H₅ | H | H | H | CH₃ | H | H | —C≡C— | 83-85 | |
| 2 | C₆H₅ | H | H | H | CH₃ | H | H | —CH=CH— | oil | trans:cis 1:2 |
| 3 | 4-Cl—C₆H₄ | H | H | H | CH₃ | H | H | —C≡C— | 130-131 | |
| 4 | 4-F—C₆H₄ | H | H | H | CH₃ | H | H | —C≡C— | | |
| 5 | 2,4-Cl₂—C₆H₃ | H | H | H | CH₃ | H | H | —C≡C— | | |
| 6 | 2-Cl—C₆H₄ | H | H | H | CH₃ | H | H | —C≡C— | 114-116 | |
| 7 | 4-CH₃O—C₆H₄ | H | H | H | CH₃ | H | H | —C≡C— | | |
| 8 | 2-CH₃O—C₆H₄ | H | H | H | CH₃ | H | H | —C≡C— | | |
| 9 | 3-Cl—C₆H₄ | H | H | H | CH₃ | H | H | —C≡C— | 116-117 | |
| 10 | 4-CH₃—C₆H₄ | H | H | H | CH₃ | H | H | —C≡C— | 160-161 | |
| 11 | 4-CF₃—C₆H₄ | H | H | H | CH₃ | H | H | —C≡C— | | |
| 12 | 4-CF₃O—C₆H₄ | H | H | H | CH₃ | H | H | —C≡C— | | |
| 13 | 4-Br—C₆H₄ | H | H | H | CH₃ | H | H | —C≡C— | | |
| 14 | 4-Cl—C₆H₄ | H | H | H | H | H | H | —C≡C— | | |
| 15 | 4-F—C₆H₄ | H | H | H | H | H | H | —C≡C— | | |
| 16 | 2,4-Cl₂—C₆H₃ | H | H | H | H | H | H | —C≡C— | | |
| 17 | 2-Cl—C₆H₄ | H | H | H | H | H | H | —C≡C— | | |
| 18 | 4-CH₃O—C₆H₄ | H | H | H | H | H | H | —C≡C— | | |
| 19 | 2-CH₃O—C₆H₄ | H | H | H | H | H | H | —C≡C— | | |
| 20 | 3-Cl—C₆H₄ | H | H | H | H | H | H | —C≡C— | | |
| 21 | 4-CH₃—C₆H₄ | H | H | H | H | H | H | —C≡C— | | |
| 22 | 4-CF₃O—C₆H₄ | H | H | H | H | H | H | —C≡C— | | |
| 23 | 4-CF₃—C₆H₄ | H | H | H | H | H | H | —C≡C— | | |
| 24 | 4-Br—C₆H₄ | H | H | H | H | H | H | —C≡C— | | |
| 25 | 4-Cl—C₆H₄ | H | H | H | CH₃ | H | H | —CH=CH— | | cis |
| 26 | 4-F—C₆H₄ | H | H | H | CH₃ | H | H | —CH=CH— | | cis |
| 27 | 2,4-Cl₂—C₆H₃ | H | H | H | CH₃ | H | H | —CH=CH— | | cis |
| 28 | 2-Cl—C₆H₄ | H | H | H | CH₃ | H | H | —CH=CH— | | cis |
| 29 | 4-CH₃O—C₆H₄ | H | H | H | CH₃ | H | H | —CH=CH— | | cis |
| 30 | 2-CH₃O—C₆H₄ | H | H | H | CH₃ | H | H | —CH=CH— | | cis |
| 31 | 3-Cl—C₆H₄ | H | H | H | CH₃ | H | H | —CH=CH— | | cis |
| 32 | 4-CH₃—C₆H₄ | H | H | H | CH₃ | H | H | —CH=CH— | | cis |
| 33 | 4-CF₃—C₆H₄ | H | H | H | CH₃ | H | H | —CH=CH— | | cis |
| 34 | 4-CF₃O—C₆H₄ | H | H | H | CH₃ | H | H | —CH=CH— | | cis |
| 35 | 4-Br—C₆H₄ | H | H | H | CH₃ | H | H | —CH=CH— | | cis |
| 36 | 4-Cl—C₆H₄ | H | H | H | CH₃ | H | H | —CH=CH— | | trans |
| 37 | 4-F—C₆H₄ | H | H | H | CH₃ | H | H | —CH=CH— | | trans |
| 38 | 2,4-Cl₂—C₆H₃ | H | H | H | CH₃ | H | H | —CH=CH— | | trans |
| 39 | 2-Cl—C₆H₄ | H | H | H | CH₃ | H | H | —CH=CH— | | trans |
| 40 | 4-CH₃O—C₆H₄ | H | H | H | CH₃ | H | H | —CH=CH— | | trans |
| 41 | 2-CH₃O—C₆H₄ | H | H | H | CH₃ | H | H | —CH=CH— | | trans |
| 42 | 3-Cl—C₆H₄ | H | H | H | CH₃ | H | H | —CH=CH— | | trans |
| 43 | 4-CH₃—C₆H₄ | H | H | H | CH₃ | H | H | —CH=CH— | | trans |
| 44 | 4-CF₃—C₆H₄ | H | H | H | CH₃ | H | H | —CH=CH— | | trans |
| 45 | 4-CF₃O—C₆H₄ | H | H | H | CH₃ | H | H | —CH=CH— | | trans |
| 46 | 4-Br—C₆H₄ | H | H | H | CH₃ | H | H | —CH=CH— | | trans |
| 47 | 4-Cl—C₆H₄ | H | H | H | H | H | H | —CH=CH— | | cis |
| 48 | 4-F—C₆H₄ | H | H | H | H | H | H | —CH=CH— | | cis |
| 49 | 2,4-Cl₂—C₆H₃ | H | H | H | H | H | H | —CH=CH— | | cis |
| 50 | 2-Cl—C₆H₄ | H | H | H | H | H | H | —CH=CH— | | cis |
| 51 | 4-CH₃O—C₆H₄ | H | H | H | H | H | H | —CH=CH— | | cis |
| 52 | 2-CH₃O—C₆H₄ | H | H | H | H | H | H | —CH=CH— | | cis |
| 53 | 3-Cl—C₆H₄ | H | H | H | H | H | H | —CH=CH— | | cis |
| 54 | 4-CH₃—C₆H₄ | H | H | H | H | H | H | —CH=CH— | | cis |
| 55 | 4-CF₃—C₆H₄ | H | H | H | H | H | H | —CH=CH— | | cis |
| 56 | 4-CF₃O—C₆H₄ | H | H | H | H | H | H | —CH=CH— | | cis |
| 57 | 4-Br—C₆H₄ | H | H | H | H | H | H | —CH=CH— | | cis |
| 58 | 4-Cl—C₆H₄ | H | H | H | H | H | H | —CH=CH— | | trans |
| 59 | 4-F—C₆H₄ | H | H | H | H | H | H | —CH=CH— | | trans |
| 60 | 2,4-Cl₂—C₆H₃ | H | H | H | H | H | H | —CH=CH— | | trans |
| 61 | 2-Cl—C₆H₄ | H | H | H | H | H | H | —CH=CH— | | trans |
| 62 | 4-CH₃O—C₆H₄ | H | H | H | H | H | H | —CH=CH— | | trans |
| 63 | 2-CH₃O—C₆H₄ | H | H | H | H | H | H | —CH=CH— | | trans |
| 64 | 3-Cl—C₆H₄ | H | H | H | H | H | H | —CH=CH— | | trans |
| 65 | 4-CH₃—C₆H₄ | H | H | H | H | H | H | —CH=CH— | | trans |
| 66 | 4-CF₃—C₆H₄ | H | H | H | H | H | H | —CH=CH— | | trans |
| 67 | 4-CF₃O—C₆H₄ | H | H | H | H | H | H | —CH=CH— | | trans |

TABLE I-continued

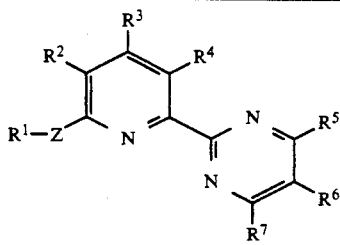

| Compound No | R¹ | R² | R³ | R⁴ | R⁵ | R⁶ | R⁷ | Z | mp °C. | Comments |
|---|---|---|---|---|---|---|---|---|---|---|
| 68 | 4-Br—C₆H₄ | H | H | H | H | H | H | —CH=CH— | | trans |
| 69 | C₆H₅ | H | H | H | H | H | H | —CH=CH— | | cis |
| 70 | C₆H₅ | H | H | H | H | H | H | —CH=CH— | | trans |
| 71 | C₆H₅ | H | H | H | H | H | H | —CH₂—CH₂— | | |
| 72 | C₆H₅ | H | H | H | CH₃ | H | H | —CH₂—CH₂— | | |
| 73 | 4-Cl—C₆H₄ | H | H | H | H | H | H | —CH₂—CH₂— | | |
| 74 | 4-Cl—C₆H₄ | H | H | H | CH₃ | H | H | —CH₂—CH₂— | | |
| 75 | 4-F—C₆H₄ | H | H | H | H | H | H | —CH₂—CH₂— | | |
| 76 | 4-F—C₆H₄ | H | H | H | CH₃ | H | H | —CH₂—CH₂— | | |
| 77 | 2,4-Cl₂—C₆H₃ | H | H | H | H | H | H | —CH₂—CH₂— | | |
| 78 | 2,4-Cl₂—C₆H₃ | H | H | H | CH₃ | H | H | —CH₂—CH₂— | | |
| 79 | 2-Cl—C₆H₄ | H | H | H | H | H | H | —CH₂—CH₂— | | |
| 80 | 2-Cl—C₆H₄ | H | H | H | CH₃ | H | H | —CH₂—CH₂— | | |
| 81 | 4-CH₃O—C₆H₄ | H | H | H | H | H | H | —CH₂—CH₂— | | |
| 82 | 4-CH₃O—C₆H₄ | H | H | H | CH₃ | H | H | —CH₂—CH₂— | | |
| 83 | 2-CH₃O—C₆H₄ | H | H | H | H | H | H | —CH₂—CH₂— | | |
| 84 | 2-CH₃O—C₆H₄ | H | H | H | CH₃ | H | H | —CH₂—CH₂— | | |
| 85 | 3-Cl—C₆H₄ | H | H | H | H | H | H | —CH₂—CH₂— | | |
| 86 | 3-Cl—C₆H₄ | H | H | H | CH₃ | H | H | —CH₂—CH₂— | | |
| 87 | 4-CH₃—C₆H₄ | H | H | H | H | H | H | —CH₂—CH₂— | | |
| 88 | 4-CH₃—C₆H₄ | H | H | H | CH₃ | H | H | —CH₂—CH₂— | | |
| 89 | 4-CF₃—C₆H₄ | H | H | H | H | H | H | —CH₂—CH₂— | | |
| 90 | 4-CF₃—C₆H₄ | H | H | H | CH₃ | H | H | —CH₂—CH₂— | | |
| 91 | 4-CF₃O—C₆H₄ | H | H | H | H | H | H | —CH₂—CH₂— | | |
| 92 | 4-CF₃O—C₆H₄ | H | H | H | CH₃ | H | H | —CH₂—CH₂— | | |
| 93 | 4-Br—C₆H₄ | H | H | H | H | H | H | —CH₂—CH₂— | | |
| 94 | 4-Br—C₆H₄ | H | H | H | CH₃ | H | H | —CH₂—CH₂— | | |
| 95 | 3,4-Cl₂—C₆H₃ | H | H | H | CH₃ | H | H | —C≡C— | 137–139 | |
| 96 | 2,3-Cl₂—C₆H₃ | H | H | H | CH₃ | H | H | —C≡C— | 119–120.5 | |
| 97 | cyclohexyl | H | H | H | CH₃ | H | H | —C≡C— | 107.5–108.5 | |
| 98 | 4-C₆H₅—C₆H₄ | H | H | H | CH₃ | H | H | —C≡C— | 176–179° C. | |
| 99 | tert-butyl | H | H | H | Me | H | H | —C≡C— | 98–100° C. | |
| 100 | (CH₃)₃Si | H | H | H | Me | H | H | —C≡C— | | |

TABLE II

SELECTED PROTON NMR DATA

Table II shows selected proton NMR data for certain compounds described in Table I along with mass spectral data which is the molecular ion. Chemical shifts are measured in ppm from tetramethylsilane, and deuterochloroform was used as a solvent throughout.

| Compound No | NMR DATA |
|---|---|
| 1 | 2.66(3H, s); 7.19(1H, d); 7.35(3H, m); 7.62(3H, m); 7.85(1H, t); 8.45(1H, d); 8.78(1H, d) ppm. M⁺=271 |
| 2 | 2.68(3H, two singlets); 7.18(1H, d); 7.25–7.40(4H, m); 7.58–7.70(4H, m); 7.85(1H, t); 8.33–8.46(1H, dd); 8.80(1H, dd) ppm. MH⁺=274 |

The following abbreviations are used:
dd = doublet of doublets
s = singlet
d = doublet
t = triplet
m = multiplet Compounds of formula (I), wherein $R^1$, $R^2$, $R^3$, $R^4$, $R^5$, $R^6$ and $R^7$ are as defined above and Z is an acetylene (—C≡C—) linkage, can be prepared by treating a halopyridine of general formula (II), wherein $R^2$, $R^3$, $R^4$, $R^5$, $R^6$ and $R^7$ are as defined above and Hal is a halogen (preferably bromine or iodine), with an acetylene of general formula (III), wherein $R^1$ is as defined above, int he presence of a convenient palladium catalyst and cuprous iodide. The reaction si usually carried out using a base (such as diethylamine, triethylamine or piperidine) in a convenient solvent (such as tetrahydrofuran or diemthylformamide) at a temperature of 20°–100° C. Preferably the temperature of the reaction is 25° C. The usual catalyst which is used for the coupling reaction is dichlorobis(triphenylphosphine)-palladium (II).

In an alternative process compounds of formula (I), wherein Z is an acetylene (—C≡C—) linkage and $R^2$, $R^3$, $R^4$, $R^5$, $R^6$ and $R^7$ are as defined above and $R^1$ is optionally substituted phenyl, can be prepared by treating an acetylene of general formula (IV), (wherein $R^2$, $R^3$, $R^4$, $R^5$, $R^6$ and $R^7$ are as defined above, with a phenyl iodide of general formula (R¹I), (wherein $R^1$ is optionally substituted phenyl), in the presence of a convenient palladium catalyst and cuprous iodide. It is normal to carry out the reaction in the presence of an organic base (such as diethylamine or triethylamine) in a convenient solvent (such as tetrahydrofuran or dimethylformamide) at a temperature of 20°–100° C. Preferably the temperature of the reaction is 25° C. The usual palladium catalyst which is used for the coupling reaction is dichlorobis(triphenylphosphine) palladium (II).

The acetylene compound (IV) is prepared by coupling a compound of formula (II) with trimethylsilylacetylene using the already described palladium catalysis and reacting an intermediate of general formula (VI), wherein $R^2$, $R^3$, $R^4$, $R^5$, $R^6$, $R^7$ are as defined above, with potassium hydroxide in methanol as solvent at room temperature.

In a further alternative process compounds of formula (I), wherein Z is an acetylene (—C≡C—) linkage and $R^1$, $R^2$, $R^3$, $R^4$, $R^5$, $R^6$ and $R^7$ are as defined above, can be prepared by cross-coupling a bromopyridine of general formula (VII), wherein $R^1$, $R^2$, $R^3$, $R^4$ are as defined above, with a compound of formula (VIII), wherein $R^5$, $R^6$ and $R^7$ are as defined above and X is bromine or iodine. The coupling reaction can be carried out by treating the bromopyridine (VII) with normal butyl lithium in tetrahydrofuran followed by zinc chloride in diethylether, and then adding tetrakis(triphenylphosphine)palladium (0) with the compound of formula (VIII). The reaction is carried out at temperatures of between -70° and 25° C.

Compounds of formula (I), wherein Z is an olefin (—$CR^8$=$CR^{10}$—) linkage and $R^1$, $R^2$, $R^3$, $R^4$, $R^5$, $R^6$, $R^7$, $R^8$ and $R^{10}$ are as defined above, that is, compounds of general formula (IX) can be prepared by cross-coupling a vinyl halide of general formula (X), wherein $R^1$, $R^8$, $R^{10}$ are as defined above and Hal is a halogen (preferably bromine or iodine), with a halopyridine of general formula (II). The coupling reaction can be carried out by treating he halopyridine (II) with normal butyl lithium in tetrahydrofuran followed by zinc chloride in diethylether and then adding tetrakis(triphenylphosphine)palladium (0) with the vinyl halide (X). The reaction is carried out at temperatures of between —70° and 25° C.

In an alternative process for the production of compounds of general formula (IX), the above cross-coupling reaction can be carried out between a bromopyridine of general formula (XI), wherein $R^1$, $R^2$, $R^3$, $R^4$, $R^8$ and $R^{10}$ are as defined above, and a compound of formula (VIII).

Compounds of general formula (IX), wherein $R^8$ and $R^{10}$ are hydrogen can be prepared by reduction of acetylenes of general formula (XII) wherein $R^1$, $R^2$, $R^3$, $R^4$, $R^5$, $R^6$ and $R^7$ are as defined above. The reduction can either be achieved by using hydrogen with a suitable catalyst (such as palladium/calcium carbonate/lead oxide (Lindlar catalyst)) or a metal hydride reducing agent (such as lithium aluminum hydride) optionally in the presence of a transition metal catalyst. The reaction is usually carried out at 25° C.

Compounds of formula (I) wherein Z is an ethane —$CR^8R^9$—$CR^{10}R^{11}$— linkage, that is, compounds of general formula (XIII) can be prepared by cross-coupling a halo compound of general formula (XIV), wherein $R^1$, $R^8$, $R^9$, $R^{10}$, $R^{11}$ are defined above and Hal is a halogen (preferably bromine or iodine), with a halopyridine of formula (II). The coupling reaction is usually carried out by treating the halo compound (XIV) with normal butyl lithium in tetrahydrofuran followed by zinc chloride in diethyl ether, and then adding tetrakis(triphenylphosphine)palladium (0) with the halopyridine (II).

Alternatively compounds of general formula (XIII) can be prepared by cross-coupling a bromopyridine of general formula (XV), wherein $R^1$, $R^2$, $R^3$, $R^4$, $R^8$, $R^9$, $R^{10}$, $R^{11}$ are defined above, and a compound of formula (VIII).

In an alternative process compounds of general formula (XIII), wherein $R^9$ and $R^{11}$ are hydrogen, can be prepared by the reduction of compounds of general formula (IX). The reduction is preferably carried out by hydrogen in the presence of a convenient catalyst, such as palladium on carbon, in a suitable solvent, such as ethanol or ethyl acetate.

The halopyridines (II), bromopyridines (VII), compounds of formula (VIII), bromopyridines (XI) and bromopyridines (XV) are prepared by methods set out in the literature.

The salts of compounds of general formula (I) can be prepared by adding one equivalent of a strong acid such as hydrochloric acid, sulphuric acid or nitric acid, to a solution of (I) in a suitable solvent.

The present invention includes processes for preparing the compounds of formula (I) as herein defined and intermediates of formula (IV) and (VI) as herein before defined.

The compounds are active fungicides and may be used to control one or more of the following pathogens : *Pyricularia oryzae* on rice; *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants; *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; *Helminthosporium* spp., *Rhynchosporium* spp., *Septoria* spp., *Pyrenophora* spp., *Pseudocercosporella herpotrichoides* and *Gaeumannomyces graminis* on cereals; *Cercospora arachidicola* and *Cercosporidium personata* on peanuts and other *Cercospora* species on other hosts, for example, sugar beet, bananas, soya beans and rice; *Botrytis cinerea* (grey mould) on tomatoes, strawberries, vegetables, vines and other hosts; *Alternaria* spp. on vegetables (e.g. cucumber), oil-seed rape, apples, tomatoes and other hosts; *Venturia inaequalis* (scab) on apples; *Plasmopara viticola* on vines; other downy mildews such as *Bremia lactucae* on lettuce, *Peronospora* spp. on soybeans, tobacco, onions and other hosts, *Pseudoperonospora humuli* on hops and *Pseudoperonospora cubensis* on cucurbits; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including *Fusarium* spp., *Septoria* spp., *Tilletia* spp., (bunt, a seed-borne disease of wheat), *Ustilago* spp. and *Helminthosporium* spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that these compositions comprise 0.0001 to 95%, more preferably 0.001 to 60%, even more preferably 0.01 to 1%, of the compound.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid sealing.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisoPropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing .0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (±)-cis-1-(4-chlorophenyl)-2-(1H-1,2,4-triazol-1-yl)cycloheptanol, (2RS,3RS)-1-[3-(2-chlorophenyl)-2-(4-fluorophenyl)oxiran-2-ylmethyl]-1H-1,2,4-triazole, (RS)-1-aminopropylphosphonic acid, (RS)-4-(4-chlorophenyl)-2-phenyl-2-(1H-1,2,4-triazol-1-ylmethyl)-butyronitrile, (Z)-N-bu-t-2-enyloxymethyl-2-chloro-2',6'-diethylacetanilide, 1-(2-cyano-2-methoxyiminoacetyl)-3-ethyl urea, 3-(2,4-dichlorophenyl) 2-(1H-1,2,4-triazol-1-yl)quinazolin-4-(3H)-one, 4-(2,2-diiluoro-1,3-benzodioxol-4-yl)pyrrole-3-carbonitrile, 4-bromo-2-cyano-N,N-dimeth-yl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-ch-loro-2,6-xylyl)-2-methoxyacetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-be-nzyl-N-([methyl(methyl-thioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminum, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-iso-propyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb.

The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. Throughout the examples reactions involving water-sensitive intermediates were performed under atmospheres of nitrogen. Unless otherwise stated, chromatography was performed using silica gel as the stationary phase. DISPERSOL and TWEEN, where used in the Examples, are Trade or Service Marks.

EXAMPLE 1

This Example illustrates the preparation of 2-(6-phenylethynyl-2-pyridinyl)-4-methylpyrimidine (Compound No. 1 in Table I).

Stage 1

A solution of normal butyl lithium (28.6ml, 0.0714 moles of a 2.5M solution in hexane) was added dropwise to a solution of 2,6-dibromopyridine (15.8g, 0.067 moles) in dry tetrahydrofuran (100 ml) at −78° C. under a nitrogen atmosphere. The mixture was stirred for 0.5 hours at −78° C. after the addition was complete and a solution of zinc chloride (205ml, 0.2047 moles of a 1.0 M solution in diethyl ether) added dropwise so that the temperature was kept below −60° C. A white precipitate formed and the solution was stirred at −78° C. for a further 0.5 hours.

Tetrakis(triphenylphosphine)palladium (0) (1.1g, 0.00095 moles) was added, followed by 2-bromo-4-methyl-pyrimidine (8.23g, 0.0476 moles) in dry tetrahydrofuran (100 ml). After complete addition the reaction mixture was refluxed for 4 hours, cooled to room temperature, poured into a 10% solution of ethylenediamine-tetraace&is acid and extracted with methylene chloride. The combined methylene chloride extracts were washed, dried and the solvent removed to give a dark oil which was purified by column chromatography (silica gel eluted with -t-butyl methyl ether) giving 2-(6-bromo-2-pyridinyl)-4-methylpyrimidine (3.6, 30%) as a yellow solid. This was used in the next stage without further recrystallisation.

Stage 2

Copper (I) iodide (0.057g, 0.0003 moles) was added portionwise to a stirred suspension of 2-(6-bromo-2-pyridinyl)-4-methylpyrimidine (2.5g, 0.01 moles), phenylacetylene (2.04g, 0.02 moles) and dichlorobis-(triphenylphosphine)palladium (II) (0.105g, 0.00015 moles) in triethylamine (90ml) and dry tetrahydrofuran 60ml) under a nitrogen atmosphere at 20° C. The reaction mixture was stirred at room temperature for 20 hours and the solvent removed to give a dark residue. This residue was dissolved in ethyl acetate, washed and dried over anhydrous magnesium sulphate. Removal of the solvent ave a black oil which was purified by column chromatography (silia gel eluted with dichloromethane : tetrahydrofuran 98:2) to give the title compound (1.47g, 54%) as an orange solid mp 83°–85° C.

EXAMPLE 2

This Example illustrates the preparation of 2-(6-styryl-2-pyridinyl)-4-methylpyrimidine (Compound No. 2 in Table I).

Lithium aluminium hydride (0.8ml of 1.0m solution in tetrahydrofuran) was added dropwise to a mixture of 2-(6-phenylethynyl-2-pyridinyl)-4-methylpyrimidine (0.4g, 0.0015 moles) and ferrous chloride (0.15g, 0.00075 moles) in dry tetrahydrofuran (1.0 ml) at −78° C. under a nitrogen atmosphere. After complete addition, the solution was stirred at −78° C. for 0.5 hours and allowed to warm up to room temperature. The reaction mixture was poured carefully into water, extracted with ethyl acetate, washed and dried over anhydrous magnesium sulphate. Removal of the solvent gave a brown oil which was purified by column chromatography (silia gel eluted with diethyl ether) to give the title compound (0.054g, 13%) as a yellow oil which is a mixture of isomers (trans:cis ratio of 1:2).

The following are examples of compositions suitable for agricultural and horticultural purposes which can be formulated from the compounds of the invention. Such compositions form another aspect of the invention. Percentages are by weight.

EXAMPLE 3

This Example illustrates the preparation of 2-(6-(4-chlorophenylethyl)pyrid-2-yl)-4-methylpyrimidine (Compound No. 3 in Table I).

Step 1

Dichlorobis(triphenylphosphine)palladium (II) (0.66g, 0.00094 moles) and copper (I) iodide (0.36g, 0.0019 moles) were added to a solution of chloro-4-iodobenzene (6.0, 0.0Z5Z moles), trimethylsilylacetylene (4.9 g, 0.0504 moles), and triethylamine (5.2 cm³, 3.8 g, 0.038 moles) in N,N-dimeth-ylformamide (60 cm³), under an atmosphere of nitrogen. The reaction was stirred, under nitrogen, at room temperature for 40 minutes, giving a dark brown mixture.

This was poured onto water (200 cm³), a 10% solution of ethylenediamine tetraacetic acid sodium salt (100 cm³) was added and the mixture was extracted with ethyl acetate (100 cm³). The organic extract was dried and the solvent removed to give a dark oil which was purified by preparative high performance liquid chromatography, (silica gel eluted with hexane) giving chloro-4-trimethylsilylethynylbenzene as a yellow solid. This was used in the next step without& further recrystallisation. Yield 3.0g (58%). ¹H NMR: 7.0 (2H,d), 7.25 (2H,d), 0.0 (not integrated but should be 9H,s)ppm.

Step 2

Anhydrous potassium carbonate (0.9g, 0.0065 moles) was added to a solution of chloro-4-trimethylsilylethynylbenzene (3.0g, 0.014 moles) in methanol (60 cm³) under an atmosphere of nitrogen. The reaction was stirred, under nitrogen, at room temperature for 4 hours. The solvent was removed, the solid residue was tritura&ed with ether and then dichloromethane and filtered. The organic filtrates were combined and evaporated to dryness giving chloro-4-ethynylbenzene as a brown solid. This was used in the next step without any further purification yield 1.1 g (58%). ¹H NMR 67.3 (2H, d), 7.4 (2H, d), 3.1 (1H, s)ppm.

Step 3

A solution of chloro-4-ethynylbenzene (0.48g, 0.0035 moles) in dry tetrahydrofuran (8cm3) was added to a solution of 2-(6-bromo-2-pyridinyl)-4-methyl pyrimidine (0.44g, 0.00176 moles) in dry tetrahydrofuran (8 cm³) under a nitrogen atmosphere. Dry triethylamine (12 cm³), dichlorobis(triphenylphosphine) palladium (II) (0.02 g, 0.000028 moles) and copper (I) iodide (99.999%) (0.02g, 0.0001 moles) were then added and the mixture was stirred at room temperature, under nitrogen, for 22 hours.

The solvent was removed and the residue was partitioned between ethyl acetate and water. The organic phase was dried and evaporated to give a brown solid residue which was purified by preparative thin layer chromatography using either as eluent. The title compound was obtained as as a pale brown solid. Yield 0.25 g (46%).

EXAMPLE 4

This Example illustrates the preparation of 2-[6-(3,3-dimethylbut-1-ynyl)-2-pyrindinyl]-4-methylpyrimidine (Compound No. 99 in Table I).

2-(6-Bromo-2-pyrindinyl)-4-methylpyrimidine (0.5 g, 0.002 moles) [prepared as in Stage 1 of Example 1] was dissolved in dry tetrahydrofuran and 3,3-dimethylbut-1-yne (0.33g, 0.004 moles) was added, followed by dry triethylamine (12 cm³), dichlorobis(triphenylphosphine)palladium (II) (0.02 g, 0.000028 moles). The reaction was left at room temperature for 17 hours then heated at 40° for 4 hours. More 3,3-trimethylbut-1-yne (0.33 g, 0.5 cm³, 0.004 moles) was added, after which the reaction mixture was heated at reflux for 2 hours and left to stand at room temperature overnight. More 3,3-dimethylbut-1-yne (0.67 g, 0.008 moles), palladium (II) catalyst (0.02 g, 0.000028 moles) and copper (I) iodide (0.01 g, 0.000053 moles) were added and reaction was heated at reflux for 3 hours. Piperidine (5 cm³) was added, giving a dark brown solution which was heated at zeflux for 1½ hours.

The mixture was evaporated to dryness under reduced pressure and the residue was partitioned between ethyl acetate and water. The organic phase was dried, then evaporated to give a dark brown viscous oil, which was purified by preparative thin layer chromotography on silica gel with ether as eluent. The title compound was obtained as a pale brown oil which solidified on standing 0.12 g, 24%, mpt 98°-100° C.).

EXAMPLE 5

An emulsifiable concentrate is made up by mixing and stirring the ingredients until all are dissolved.

| Compound No. 1 of Table I | 10% |
|---|---|
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 6

The active ingredient is dissolved in methylene dichloride and the resultant liquid sprayed on to the granules of attapulgite clay. The solvent is then allowed to evaporate to produce a granular composition.

| Compound No. 2 of Table I | 5% |
|---|---|
| Attapulgite granules | 95% |

EXAMPLE 7

A composition suitable for use as a seed dressing is prepared by grinding and mixing the three ingredients.

| Compound No. 1 of Table I | 50% |
|---|---|
| Mineral oil | 2% |
| China clay | 48% |

EXAMPLE 8

A dustable powder is prepared by grinding and mixing the active ingredient with talc.

| Compound No. 1 of Table I | 5% |
|---|---|
| Talc | 95% |

EXAMPLE 9

A suspension concentrate is prepared by ball milling the ingredients to form an aqueous suspension of the ground mixture with water.

| Compound No. 1 of Table I | 40% |
|---|---|
| Sodium lignosulphonate | 10% |
| Bentonite Clay | 1% |
| Water | 49% |

This formulation can be used as a spray by diluting into water or applied directly to seed.

EXAMPLE 10

A wettable powder formulation is made by mixing together and grinding the ingredients until all are throughly mixed.

| Compound No. 1 of Table I | 25% |
|---|---|
| Sodium lauryl sulphate | 2% |
| Sodium lignosulphonate | 5% |
| Silica | 25% |
| China clay | 43% |

EXAMPLE 11

The compounds were tested against a variety of foliar fungal diseases of plants. The technique employed was as follows.

The plants were grown in John Innes Potting Compost (No 1 or 2) in 4 cm diameter minipots. The test compounds were formulated by bead milling with aqueous DISPERSOL T which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. TWEEN 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on Erysiphe graminis in which the plants were inoculated 24 hours before treatment. Foliar Pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace −5% of disease on untreated plants
2 = 6-25% of disease on untreated plants
1 = 6-59% of disease on untreated plants
0 = 60-100% of disease on untreated plants
The results are shown in Table III.

TABLE III

| Compound No | Puccinia recondita (Wheat) | Erysiphe graminis tritici (Wheat) | Venturia inaequalis (Apple) | Pyricularia oryzae (Rice) | Thanetophorus cucumberis (Rice) | Septoria nodorum | Plasmopara viticola (Vine) |
|---|---|---|---|---|---|---|---|
| 1 | 3 | 4 | 4 | 4 | — | 0 | 1 |
| 2 | 0* | 0* | 4* | 3* | — | 3* | 0* |
| 3 | — | 2 | 2 | 4 | 0 | 0 | 3 |

TABLE III-continued

| Compound No | Puccinia recondita (Wheat) | Erysiphe graminis tritici (Wheat) | Venturia inaequalis (Apple) | Pyricularia oryzae (Rice) | Thanetophorus cucumberis (Rice) | Septoria nodorum | Plasmopara viticola (Vine) |
|---|---|---|---|---|---|---|---|
| 6 | — | 0 | 4 | 4 | 0 | 0 | 1 |
| 10 | 0 | 0 | 0 | 1 | 0 | 0 | 2 |
| 95 | — | 0 | 1 | 2 | 0 | 0 | 4 |
| 96 | — | 0 | 3 | 3 | 0 | 3 | 4 |
| 97 | 0 | 0 | 4 | 3 | 1 | 0 | 3 |

*data generated at 25 ppm.

We claim:

1. A compound of formula (I):

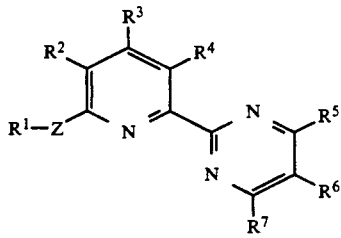

wherein $R^1$ is an optional substituted phenyl with one or more members of the group consisting of halogen, $C_{1-4}$ alkyl, $C_{1-4}$ alkoxy, $C_{1-4}$ haloalkoxy, $C_{2-4}$ alkenyl, $C_{2-4}$ alkynyl, $C_{1-4}$ haloalkyl and phenyl, $C_{3-6}$ cycloalkyl optionally substituted by alkyl; $R^2$, $R^3$, $R^4$, $R^5$, $R^6$ and $R^7$ are independently hydrogen, $C_{1-4}$ alkyl, $C_{1-4}$ haloalkyl, $C_{1-4}$ alkoxy or $NR'R''$; Z is a linking group and is $-C\equiv C-$, $-CR^8=CR^{10}-$ or $-CR^8R^9-CR^{10}CR^{11}-$; $R^8$, $R^9$, $R^{10}$, $R^{11}$, $R'$ and $R''$ are independently hydrogen or $C_{1-4}$ alkyl; provided that when $R^1$ is alkyl Z is not $-CR^8R^9-CR^{10}CR^{11}-$; and acid addition salts or metal complexes thereof.

2. A compound of claim 1 of formula (I):

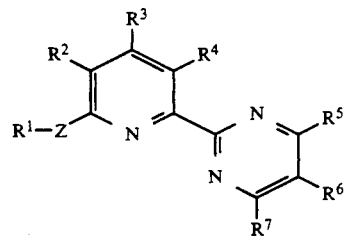

wherein $R^1$ is an optionally substituted phenyl group; $R^2$, $R^3$, $R^4$, $R^5$, $R^6$ and $R^7$ are independently hydrogen, $C_{1-04}$ alkyl, $C_{1-4}$ haloalkyl or $C_{1-4}$ alkoxy; Z is a linking group and is $-C\equiv C-$, $-CR^8=CR^{10}-$ or $-CR^8-R^9-CR^{10}R^{11}-$; $R^8$, $R^9$, $R^{10}$ and $R^{11}$ are independently hydrogen or $C_{1-4}$ alkyl; and acid additions salts or metal complexes thereof.

3. A compound as claimed in claim 1 or 2 having the formula (I):

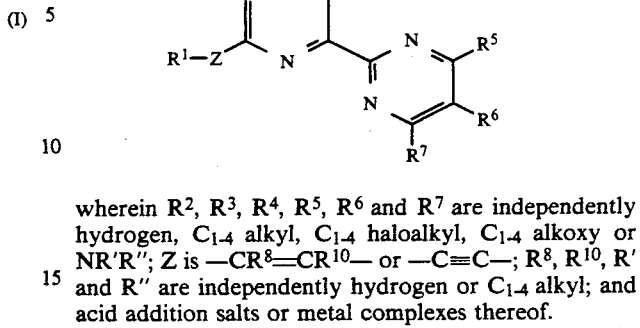

wherein $R^2$, $R^3$, $R^4$, $R^5$, $R^6$ and $R^7$ are independently hydrogen, $C_{1-4}$ alkyl, $C_{1-4}$ haloalkyl, $C_{1-4}$ alkoxy or $NR'R''$; Z is $-CR^8=CR^{10}-$ or $-C\equiv C-$; $R^8$, $R^{10}$, $R'$ and $R''$ are independently hydrogen or $C_{1-4}$ alkyl; and acid addition salts or metal complexes thereof.

4. A compound as claimed in claim 1, 2 or 3 wherein $R^2$, $R^3$, $R^4$, $R^6$ and $R^7$ are all hydrogen and $R^5$ is $C_{1-4}$ alkyl.

5. A compound as claimed in claims 1, 2, 3 or 4 having the formula (I):

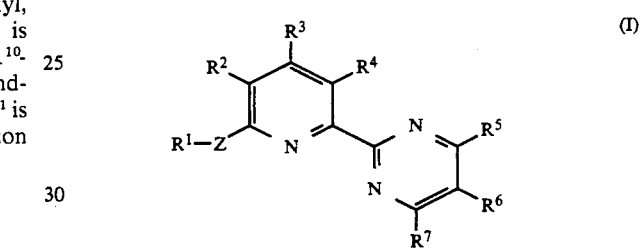

wherein $C_{1-4}$ haloalkyl and phenyl; Z is $-C\equiv C-$; $R^2$, $R^3$, $R^4$, $R^6$ and $R^7$ are all hydrogen; $R^5$ is $C_{1-4}$ alkyl; and acid addition salts or metal complexes thereof.

6. A compound as claimed in claim 1 or 2 having the formula (I):

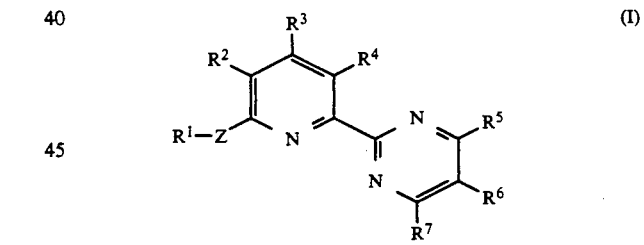

wherein $R^1$ is phenyl optionally substituted with halogen, $C_{1-4}$ alkyl, $C_{1-4}$ haloalkoxy or phenyl, or $R^1$ is cyclohexyl or tert-butyl; Z $-CH=Ch-$ or $-C\equiv C-$; $R^2$, $R^3$, $R^4$, $R^6$ and $R^7$ are all hydrogen; and $R^5$ is $C_{1-4}$ alkyl.

7. A fungicidal composition comprising a fungicidally effective amount of a compound according to claim 1 and a fungicidally acceptable carrier or diluent therefor.

8. A method of combating fungi which comprises applying to plants, to the seeds of plant or to the locus of the plants or seeds, a compound according to claim 1 or a composition according to claim 7.

* * * * *